(12) United States Patent
Wang et al.

(10) Patent No.: US 7,598,198 B2
(45) Date of Patent: Oct. 6, 2009

(54) RHODIUM CONTAINING CATALYSTS

(75) Inventors: Tao Wang, Houston, TX (US); Leslie Wade, Pearland, TX (US); Ioan Nicolau, Corpus Christi, TX (US); Yumin Liu, San Jose, CA (US); Victor Wong, San Jose, CA (US); Barbara Kimmich, League City, TX (US); Jun Han, Sunnyvale, CA (US); Valery Sokolovskii, Sunnyvale, CA (US); Alfred Hagemeyer, Rheine (DE); David M. Lowe, Sunnyvale, CA (US); Karin Yaccato, Cambridge, MA (US); Anthony Volpe, Santa Clara, CA (US)

(73) Assignee: Calanese International Corp., Dallas, TX (US)

( * ) Notice: Subject to any disclaimer, the term of this patent is extended or adjusted under 35 U.S.C. 154(b) by 0 days.

(21) Appl. No.: 12/183,247

(22) Filed: Jul. 31, 2008

(65) Prior Publication Data

US 2008/0287285 A1 Nov. 20, 2008

Related U.S. Application Data

(62) Division of application No. 10/993,507, filed on Nov. 19, 2004.

(60) Provisional application No. 60/531,415, filed on Dec. 19, 2003, provisional application No. 60/530,936, filed on Dec. 19, 2003, provisional application No. 60/531,486, filed on Dec. 19, 2003, provisional application No. 60/530,937, filed on Dec. 19, 2003.

(51) Int. Cl.
| | |
|---|---|
| *B01J 31/04* | (2006.01) |
| *B01J 37/08* | (2006.01) |
| *B01J 23/40* | (2006.01) |
| *B01J 23/52* | (2006.01) |
| *B01J 23/58* | (2006.01) |
| *C08F 4/603* | (2006.01) |

(52) U.S. Cl. .................. 502/107; 502/113; 502/325; 502/330

(58) Field of Classification Search ............. 502/107, 502/113, 325, 330
See application file for complete search history.

(56) References Cited

U.S. PATENT DOCUMENTS

| | | | |
|---|---|---|---|
| 3,441,601 A | 4/1969 | Sennewald et al. | |
| 3,470,230 A | 9/1969 | Hirsch et al. | |
| 3,775,342 A | 11/1973 | Kronig et al. | |
| 3,822,308 A | 7/1974 | Kronig et al. | |
| 4,087,622 A | 5/1978 | Nakamura et al. | |
| 4,340,504 A | 7/1982 | Courty et al. | |
| 4,420,420 A | 12/1983 | Mita et al. | |
| 4,764,498 A | 8/1988 | Wissner et al. | |
| 4,902,823 A | 2/1990 | Wunder et al. | |
| 4,977,126 A | 12/1990 | Mauldin et al. | |
| 5,185,308 A | 2/1993 | Bartley et al. | |
| 5,194,417 A | 3/1993 | Smith et al. | |
| 5,200,382 A | 4/1993 | Cody et al. | |
| 5,274,181 A | 12/1993 | Bartley et al. | |
| 5,314,858 A | 5/1994 | Colling | |
| 5,332,710 A | 7/1994 | Nicolau et al. | |
| 5,336,802 A | 8/1994 | Smith et al. | |
| 5,342,987 A | 8/1994 | Bartley | |
| 5,466,652 A | 11/1995 | Paparizos et al. | |
| 5,559,071 A | 9/1996 | Abel et al. | |
| 5,567,839 A | 10/1996 | Gulliver et al. | |
| 5,576,457 A | 11/1996 | Abel | |
| 5,691,267 A | 11/1997 | Nicolau et al. | |
| 5,700,753 A | 12/1997 | Wang et al. | |
| 5,705,679 A * | 1/1998 | Nicolau et al. | ............... 560/245 |
| 5,808,136 A | 9/1998 | Tacke et al. | |
| 5,859,287 A | 1/1999 | Nicolau et al. | |
| 5,935,889 A | 8/1999 | Murrell et al. | |
| 5,990,344 A | 11/1999 | Couves et al. | |
| 6,015,769 A | 1/2000 | Wang | |
| 6,017,847 A | 1/2000 | Wang | |
| 6,022,823 A | 2/2000 | Augustine et al. | |
| 6,034,030 A | 3/2000 | Nicolau et al. | |
| 6,057,260 A | 5/2000 | Nicolau et al. | |
| 6,107,513 A | 8/2000 | Herzog et al. | |
| 6,107,514 A | 8/2000 | Nicolau et al. | |
| 6,114,571 A | 9/2000 | Abel et al. | |
| 6,114,573 A | 9/2000 | Herzog | |
| 6,143,921 A | 11/2000 | Karim et al. | |

(Continued)

FOREIGN PATENT DOCUMENTS

AU 2004311903 B2 7/2005

(Continued)

*Primary Examiner*—Timothy C Vanoy
*Assistant Examiner*—Daniel Berns
(74) *Attorney, Agent, or Firm*—Simmons Perrine Moyer Bergman PLC

(57) ABSTRACT

The present invention addresses at least four different aspects relating to catalyst structure, methods of making those catalysts and methods of using those catalysts for making alkenyl alkanoates. Separately or together in combination, the various aspects of the invention are directed at improving the production of alkenyl alkanoates and VA in particular, including reduction of by-products and improved production efficiency. A first aspect of the present invention pertains to a unique palladium/gold catalyst or pre-catalyst (optionally calcined) that includes rhodium or another metal. A second aspect pertains to a palladium/gold catalyst or pre-catalyst that is based on a layered support material where one layer of the support material is substantially free of catalytic components. A third aspect pertains to a palladium/gold catalyst or pre-catalyst on a zirconia containing support material. A fourth aspect pertains to a palladium/gold catalyst or pre-catalyst that is produced from substantially chloride free catalytic components.

23 Claims, No Drawings

U.S. PATENT DOCUMENTS

| | | | |
|---|---|---|---|
| 6,156,927 | A | 12/2000 | Halcom et al. |
| 6,225,496 | B1 | 5/2001 | Baker et al. |
| 6,258,978 | B1 | 7/2001 | Kitchen et al. |
| 6,268,522 | B1 | 7/2001 | Hagemeyer et al. |
| 6,303,537 | B1 | 10/2001 | Wang et al. |
| 6,342,628 | B1 | 1/2002 | Williams et al. |
| 6,346,501 | B1 | 2/2002 | Herzog et al. |
| 6,350,900 | B1 | 2/2002 | Wang et al. |
| 6,350,901 | B1 | 2/2002 | Kitchen et al. |
| 6,358,882 | B1 | 3/2002 | Salem et al. |
| 6,376,706 | B2 | 4/2002 | Kitchen et al. |
| 6,399,813 | B1 | 6/2002 | Blum et al. |
| 6,407,283 | B2 | 6/2002 | Couves et al. |
| 6,420,308 | B1 | 7/2002 | Khanmamedova |
| 6,448,432 | B2 | 9/2002 | Williams |
| 6,472,556 | B2 | 10/2002 | Kitchen et al. |
| 6,486,093 | B2 | 11/2002 | Wang et al. |
| 6,486,370 | B1 | 11/2002 | Rende et al. |
| 6,492,299 | B1 | 12/2002 | Couves et al. |
| 6,603,038 | B1 | 8/2003 | Hagemeyer et al. |
| 2001/0048970 | A1 | 12/2001 | Hagemeyer et al. |
| 2002/0013220 | A1 | 1/2002 | Wang et al. |
| 2002/0016495 | A1 | 2/2002 | Williams |
| 2002/0058833 | A1 | 5/2002 | Cirjak et al. |
| 2002/0188152 | A1 | 12/2002 | Khanmamedova |
| 2002/0198404 | A1 | 12/2002 | Herzog et al. |
| 2003/0059356 | A1 | 3/2003 | Hoke et al. |
| 2003/0109746 | A1 | 6/2003 | Fiorentino et al. |
| 2003/0148883 | A1 | 8/2003 | Khanmamedova |
| 2003/0161775 | A1 | 8/2003 | Rodemerck et al. |
| 2003/0166466 | A1 | 9/2003 | Hoke et al. |

FOREIGN PATENT DOCUMENTS

| | | |
|---|---|---|
| CA | 820352 | 8/1969 |
| DE | 19914066 A1 | 10/2000 |
| DE | 10030039 A1 | 1/2002 |
| EP | 0347830 A2 | 6/1989 |
| EP | 0569624 | 11/1993 |
| EP | 0634208 | 7/1994 |
| EP | 0634209 | 7/1994 |
| EP | 0654301 | 5/1995 |
| EP | 0672453 | 9/1995 |
| EP | 0685449 | 12/1995 |
| EP | 0685451 | 12/1995 |
| EP | 0871064 | 5/1996 |
| EP | 0891226 | 3/1997 |
| EP | 0847982 | 6/1998 |
| EP | 0997192 | 9/1998 |
| EP | 0891224 | 1/1999 |
| EP | 0898494 | 3/1999 |
| EP | 1015108 | 6/2001 |
| EP | 0723810 | 7/2001 |
| EP | 0906151 | 7/2001 |
| EP | 0874798 | 8/2001 |
| EP | 0986433 | 8/2001 |
| EP | 0877727 | 11/2001 |
| EP | 0909213 | 11/2001 |
| EP | 1164123 | 12/2001 |
| EP | 0827422 | 2/2002 |
| EP | 0839793 | 3/2002 |
| EP | 1230977 | 8/2002 |
| EP | 1102635 | 10/2002 |
| EP | 1106247 | 3/2003 |
| EP | 1323469 | 7/2003 |
| JP | 10139727 | 5/1998 |
| JP | 10195021 | 7/1998 |
| JP | 10328571 | 12/1998 |
| JP | 11009997 | 1/1999 |
| JP | 11244696 | 9/1999 |
| JP | 11244697 | 9/1999 |
| JP | 11268017 | 10/1999 |
| JP | 11349534 | 12/1999 |
| JP | 2000169430 | 12/1999 |
| JP | 2000000473 | 1/2000 |
| JP | 2000063324 | 2/2000 |
| JP | 2000063325 | 2/2000 |
| JP | 2000063326 | 2/2000 |
| JP | 2000086335 | 3/2000 |
| JP | 2000119219 | 4/2000 |
| JP | 2000176285 | 6/2000 |
| JP | 2000218152 | 8/2000 |
| JP | 2002030036 | 6/2001 |
| JP | 10081508 | 3/2008 |
| WO | WO 94/21374 | 9/1994 |
| WO | WO 97/33690 | 9/1997 |
| WO | WO 97/36678 | 10/1997 |
| WO | WO 97/36679 | 10/1997 |
| WO | WO 97/37759 | 10/1997 |
| WO | WO 97/38790 | 10/1997 |
| WO | WO 97/44130 | 11/1997 |
| WO | WO 98/00232 | 1/1998 |
| WO | WO 98/05620 | 2/1998 |
| WO | WO 98/52688 | 11/1998 |
| WO | WO 98/55225 | 12/1998 |
| WO | WO 98/55443 | 12/1998 |
| WO | WO 99/08790 | 2/1999 |
| WO | WO 99/21650 | 5/1999 |
| WO | WO 99/22863 | 5/1999 |
| WO | WO 99/29418 | 6/1999 |
| WO | WO 99/29419 | 6/1999 |
| WO | WO 99/30818 | 6/1999 |
| WO | WO 99/39824 | 8/1999 |
| WO | WO 99/42212 | 8/1999 |
| WO | WO 99/51339 | 10/1999 |
| WO | WO 99/62632 | 12/1999 |
| WO | WO 99/62633 | 12/1999 |
| WO | WO 99/62634 | 12/1999 |
| WO | WO 00/07727 | 2/2000 |
| WO | WO 00/44496 | 8/2000 |
| WO | WO 00/51962 | 9/2000 |
| WO | WO 00/58008 | 10/2000 |
| WO | WO 00/66261 | 11/2000 |
| WO | WO 00/69802 | 11/2000 |
| WO | WO 01/00559 | 1/2001 |
| WO | WO 01/07496 | 2/2001 |
| WO | WO 01/36091 | 5/2001 |
| WO | WO 01/36092 | 5/2001 |
| WO | WO 01/90042 | 11/2001 |
| WO | WO 01/90043 | 11/2001 |
| WO | WO 02/04392 | 1/2002 |

* cited by examiner

RHODIUM CONTAINING CATALYSTS

CLAIM OF PRIORITY

The present application is a divisional of Ser. No. 10/993,507, filed on Nov. 19, 2004, which claims the benefit of U.S. provisional applications 60/531,415; 60/530,936; 60/531,486; and 60/530,937, all filed on Dec. 19, 2003, all of which are hereby incorporated by reference.

FIELD OF THE INVENTION

The present invention relates to catalysts, methods of making the catalysts, and methods of making alkenyl alkanoates. More particularly, the invention relates to methods of making vinyl acetate.

BACKGROUND OF THE INVENTION

Certain alkenyl alkanoates, such as vinyl acetate (VA), are commodity chemicals in high demand in their monomer form. For example, VA is used to make polyvinyl acetate (PVAc), which is used commonly for adhesives, and accounts for a large portion of VA use. Other uses for VA included polyvinyl alcohol (PVOH), ethylene vinyl acetate (EVA), vinyl acetate ethylene (VAE), polyvinyl butyral (PVB), ethylene vinyl alcohol (EVOH), polyvinyl formal (PVF), and vinyl chloride-vinyl acetate copolymer. PVOH is typically used for textiles, films, adhesives, and photosensitive coatings. Films and wire and cable insulation often employ EVA in some proportion. Major applications for vinyl chloride-vinyl acetate copolymer include coatings, paints, and adhesives often employ VAE having VA in some proportion. VAE, which contains more than 50 percent VA, is primarily used as cement additives, paints, and adhesives. PVB is mainly used for under layer in laminated screens, coatings, and inks. EVOH is used for barrier films and engineering polymers. PVF is used for wire enamel and magnetic tape.

Because VA is the basis for so many commercially significant materials and products, the demand for VA is large, and VA production is frequently done on a relatively large scale, e.g. 50,000 metric tons or more per year. This large scale production means that significant economies of scale are possible and relatively subtle changes in the process, process conditions or catalyst characteristics can have a significant economic impact on the cost of the production of VA.

Many techniques have been reported for the production of alkenyl alkanoates. For example, in making VA, a widely used technique includes a catalyzed gas phase reaction of ethylene with acetic acid and oxygen, as seen in the following reaction:

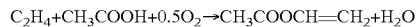

$$C_2H_4+CH_3COOH+0.5O_2 \rightarrow CH_3COOCH=CH_2+H_2O$$

Several side reactions may take place, including, such as, the formation of $CO_2$. The results of this reaction are discussed in terms of the space-time yield (STY) of the reaction system, where the STY is the grams of VA produced per liter of catalyst per hour of reaction time (g/l*h).

The composition of the starting material feed can be varied within wide limits. Typically, the starting material feed includes 30-70% ethylene, 10-30% acetic acid and 4-16% oxygen. The feed may also include inert materials such as $CO_2$, nitrogen, methane, ethane, propane, argon and/or helium. The primary restriction on feed composition is the oxygen level in the effluent stream exiting the reactor must be sufficiently low such that the stream is outside the flammability zone. The oxygen level in the effluent is affected by the oxygen level in the starting material stream, $O_2$ conversion rate of the reaction and the amount of any inert material in the effluent.

The gas phase reaction has been carried out where a feed of the starting materials is passed over or through fixed bed reactors. Successful results have been obtained through the use of reaction temperatures in the range of −125° C. to 200° C., while reaction pressures of 1-15 atmospheres are typical.

While these systems have provided adequate yields, there continues to be a need for reduced production of by-products, higher rates of VA output, and lower energy use during production. One approach is to improve catalyst characteristics, particularly as to $CO_2$ selectivity and/or activity of the catalyst. Another approach is to modify reaction conditions, such as the ratio of starting materials to each other, the $O_2$ conversion of the reaction, the space velocity (SV) of the starting material feed, and operating temperatures and pressures.

The formation of $CO_2$ is one aspect which may be reduced through the use of improved catalysts. The $CO_2$ selectivity is the percentage of the ethylene converted that goes to $CO_2$. Decreasing the $CO_2$ selectivity permits a larger amount of VA per unit volume and unit time in existing plants, even retaining all other reaction conditions.

VA output of a particular reaction system is affected by several other factors including the activity of the catalyst, the ratio of starting materials to each other, the $O_2$ conversion of the reaction, the space velocity (SV) of the starting material feed, and operating temperatures and pressures. All these factors cooperate to determine the space-time yield (STY) of the reaction system, where the STY is discussed in terms of grams of VA produced per liter of catalyst per hour of reaction time or g/l*h.

Generally, activity is a significant factor in determining the STY, but other factors may still have a significant impact on the STY. Typically, the higher the activity of a catalyst, the higher the STY the catalyst is able to produce.

The O2 conversion is a measure of how much oxygen reacts in the presence of the catalyst. The $O_2$ conversion rate is temperature dependent such that the conversion rate generally climbs with the reaction temperature. However, the amount of $CO_2$ produced also increases along with the $O_2$ conversion. Thus, the $O_2$ conversion rate is selected to give the desired VA output balanced against the amount of $CO_2$ produced. A catalyst with a higher activity means that the overall reaction temperature can be lowered while maintaining the same O2 conversion. Alternatively, a catalyst with a higher activity will give a higher $O_2$ conversion rate at a given temperature and space velocity.

It is common that catalysts employ one or more catalytic components carried on a relatively inert support material. In the case of VA catalysts, the catalytic components are typically a mixture of metals that may be distributed uniformly throughout the support material ("all through-out catalysts"), just on the surface of the support material ("shell catalysts"), just below a shell of support material ("egg white catalysts") or in the core of the support material ("egg yolk catalysts").

Numerous different types of support materials have been suggested for use in VA catalyst including silica, cerium doped silica, alumina, titania, zirconia and oxide mixtures. But very little investigation of the differences between the support materials has been done. For the most part, only silica and alumina have actually been commercialized as support materials.

One useful combination of metals for VA catalysis is palladium and gold. Pd/Au catalysts provide adequate $CO_2$ selectivity and activity, but there continues to be a need for improved catalysts given the economies of scale that are possible in the production of VA.

One process for making Pd/Au catalysts typically includes the steps of impregnating the support with aqueous solutions of water-soluble salts of palladium and gold; reacting the impregnated water-soluble salts with an appropriate alkaline compound e.g., sodium hydroxide, to precipitate (often called fixing) the metallic elements as water-insoluble compounds, e.g. the hydroxides; washing the fixed support material to remove un-fixed compounds and to otherwise cleanse the catalyst of any potential poisons, e.g. chloride; reducing the water insoluble compounds with a typical reductant such as hydrogen, ethylene or hydrazine, and adding an alkali metal compound such as potassium or sodium acetate.

Various modifications to this basic process have been suggested. For example, in U.S. Pat. No. 5,990,344, it is suggested that sintering of the palladium be undertaken after the reduction to its free metal form. In U.S. Pat. No. 6,022,823, it suggested that calcining the support in a non-reducing atmosphere after impregnation with both palladium and gold salts might be advantageous. In WO94/21374, it is suggested that after reduction and activation, but before its first use, the catalyst may be pretreated by successive heating in oxidizing, inert, and reducing atmospheres.

In U.S. Pat. No. 5,466,652, it is suggested that salts of palladium and gold that are hydroxyl-, halide- and barium-free and soluble in acetic acid may be useful to impregnate the support material. A similar suggestion is made in U.S. Pat. No. 4,902,823, i.e. use of halide- and sulfur-free salts and complexes of palladium soluble in unsubstituted carboxylic acids having two to ten carbons.

In U.S. Pat. No. 6,486,370, it suggested that a layered catalyst may be used in a dehydrogenation process where the inner layer support material differs from the outer layer support material. Similarly, U.S. Pat. No. 5,935,889 suggests that a layered catalyst may useful as acid catalysts. But neither suggests the use of layered catalysts in the production of alkenyl alkanoates.

Taken together, the inventors have recognized and addressed the need for continued improvements in the field of VA catalysts to provide improved VA production at lower costs.

SUMMARY OF THE INVENTION

The present invention addresses at least four different aspects relating to catalyst structure, methods of making those catalysts and methods of using those catalysts for making alkenyl alkanoates. Separately or together in combination, the various aspects of the invention are directed at improving the production of alkenyl alkanoates and VA in particular, including reduction of by-products and improved production efficiency. A first aspect of the present invention pertains to a unique palladium/gold catalyst or pre-catalyst (optionally calcined) that includes rhodium or another metal. A second aspect pertains to a palladium/gold catalyst or pre-catalyst that is based on a layered support material where one layer of the support material is substantially free of catalytic components. A third aspect pertains to a palladium/gold catalyst or pre-catalyst on a zirconia containing support material. A fourth aspect pertains to a palladium/gold catalyst or pre-catalyst that is produced from substantially chloride free catalytic components.

DETAILED DESCRIPTION

Catalysts

For present purposes, a catalyst is any support material that contains at least one catalytic component and that is capable of catalyzing a reaction, whereas a pre-catalyst is any material that results from any of the catalyst preparation steps discussed herein.

Catalysts and pre-catalysts of the present invention may include those having at least one of the following attributes: 1) the catalyst will be a palladium and gold containing catalyst that includes at least another catalytic component, e.g. rhodium where the one or more of the catalytic components have been calcined; 2) the catalyst will be carried on a layered support, 3) the catalyst will be carried on a zirconia containing support material; 4) the catalyst will be produced with chloride free precursors or any combination of the foregoing. Effective use of the catalyst accordingly should help improve $CO_2$ selectivity, activity or both, particularly as pertaining to VA production.

It should be appreciated that the present invention is described in the context of certain illustrative embodiments, but may be varied in any of a number of aspects depending on the needs of a particular application. By way of example, without limitation, the catalysts may have the catalytic components uniformly distributed throughout the support material or they may be shell catalysts where the catalytic components are found in a relatively thin shell around a support material core. Egg white catalysts may also be suitable, where the catalytic components reside substantially away from the center of support material. Egg yolk catalysts may also be suitable.

Catalytic Components

In general, the catalysts and pre-catalysts of the present invention include metals and particularly include a combination of at least two metals. In particular, the combination of metals includes at least one from Group VIIIB and at least one from Group IB. It will be appreciated that "catalytic component" is used to signify the metal that ultimately provides catalytic functionally to the catalyst, but also includes the metal in a variety of states, such as salt, solution, sol-gel, suspensions, colloidal suspensions, free metal, alloy, or combinations thereof. Preferred catalysts include palladium and gold as the catalytic components.

One embodiment of the catalyst includes a combination of catalytic components having palladium and gold combined with a third catalytic component. The third catalytic component is preferably selected from Group VIIIB, with Rh being the most preferred. Other preferred catalysts include those where the third catalytic component is selected from W, Ni, Nb, Ta, Ti, Zr, Y, Re, Os, Fe, Cu, Co, Zn, In, Sn, Ce, Ge, Ga and combinations thereof.

Another embodiment of the catalyst includes a combination of catalytic components including proportions of palladium, gold, and rhodium. Optionally a third catalytic component (as listed above) may also be included in this embodiment in place of Rh. In another embodiment, two or more catalytic components from the above list may be employed.

In one example, palladium and gold may be combined with Rh to form a catalyst that shows improved $CO_2$ selectively (i.e. decreased formation of $CO_2$) compared to Pd/Au catalysts that lack Rh. Also, the addition of Rh does not appear to adversely affect the activity of the catalyst. The $CO_2$ selectivity of the palladium, gold, rhodium catalyst may also be improved through calcining during the catalyst preparation and/or through the use of water-soluble halide free precursors (both discussed below), although these are not necessary to observe the Rh effect The atomic ratio of the third catalytic component to palladium may be in the range of about 0.005 to about 1.0, more preferably about 0.01 to about 1.0. In one embodiment, the catalyst contains between about 0.01 and about 5.0 g of the third catalytic component per liter of catalyst.

Another preferred embodiment of the catalyst includes between about 1 to about 10 grams of palladium, and about 0.5 to about 10 grams of gold per liter of catalyst. The amount of gold is preferably from about 10 to about 125 wt % based on the weight of palladium.

In one embodiment for ground catalysts, Au to Pd atomic ratios between about 0.5 and about 1.00 may be preferred for ground catalysts. The atomic ratio can be adjusted to balance the activity and $CO_2$ selectivity. Employment of higher Au/Pd weight or atomic ratios tends to favor more active, more selective catalysts. Stated alternatively, a catalyst with an atomic ratio of about 0.6 is less selective for $CO_2$, but also has less activity than a catalyst with a ratio of about 0.8. The effect of the high Au/Pd atomic ratio on ground support material may also be enhanced through the use of relatively high excess of hydroxide ion, as discussed below with respect to the fixing step. A ground catalyst may be one where the catalytic components are contacted to the support material followed by a reduction in the particle size (e.g. by grinding or ball milling) or one where the catalytic components are contacted to the support material after the support material has been reduced in size.

For shell catalysts, the thickness of the shell of catalytic components on the support material ranges from about 5 μm to about 500 μm. More preferred ranges include from about 5 μm to about 300 μm.

Support Materials

As indicated, in one aspect of the invention, the catalytic components of the present invention generally will be carried by a support material. Suitable support materials typically include materials that are substantially uniform in identity or a mixture of materials. Overall, the support materials are typically inert in the reaction being performed. Support materials may be composed of any suitable substance preferably selected so that the support materials have a relatively high surface area per unit mass or volume, such as a porous structure, a molecular sieve structure, a honeycomb structure, or other suitable structure. For example, the support material may contain silica, alumina, silica-alumina, titania, zirconia, niobia, silicates, aluminosilicates, titanates, spinel, silicon carbide, silicon nitride, carbon, cordierite, steatite, bentonite, clays, metals, glasses, quartz, pumice, zeolites, non-zeolitic molecular sieves combinations thereof and the like. Any of the different crystalline form of the materials may also be suitable, e.g. alpha or gamma alumina. Silica and zirconia containing support materials are the most preferred. In addition, multilayer support materials are also suitable for use in the present invention.

The support material in the catalyst of this invention may be composed of particles having any of various regular or irregular shapes, such as spheres, tablets, cylinders, discs, rings, stars, or other shapes. The support material may have dimensions such as diameter, length or width of about 1 to about 10 mm, preferably about 3 to about 9 mm. In particular having a regular shape (e.g. spherical) will have as its preferred largest dimension of about 4 mm to about 8 mm. In addition, a ground or powder support material may be suitable such that the support material has a regular or irregular shape with a diameter of between about 10 microns and about 1000 micron, with preferred sizes being between about 10 and about 700 microns, with most preferred sizes being between about 180 microns and about 450 microns. Larger or smaller sizes may be employed, as well as polydisperse collections of particles sizes. For example, for a fluid bed catalyst a preferred size range would include 10 to 150 microns. For precursors used in layered catalysts, a size range of 10 to 250 microns is preferred.

Surface areas available for supporting catalytic components, as measured by the BET (Brunauer, Emmett, and Teller) method, may generally be between about 1 $m^2/g$ and about 500 $m^2/g$, preferably about 100 $m^2/g$ to about 200 $m^2/g$. For example, for a porous support, the pore volume of the support material may generally be about 0.1 to about 2 ml/g, and preferably about 0.4 to about 1.2 ml/g. An average pore size in the range, for example, of about 50 to about 2000 angstroms is desirable, but not required.

Examples of suitable silica containing support materials include KA160 from Sud Chemie, Aerolyst350 from Degussa and other pyrogenic or microporous-free silicas with a particle size of about 1 mm to about 10 mm.

Examples of suitable zirconia containing support materials include those from Nor Pro, Zirconia Sales (America), Inc., Daichi Kigenso Kagaku Kogyo, and Magnesium Elektron Inc (MEI). Suitable zirconia support materials have a wide range of surface areas from less than about 5 $m^2/g$ to more than 300 $m^2/g$. Preferred zirconia support materials have surface areas from about 10 $m^2/g$ to about 135 $m^2/g$. Support materials may have their surfaces treated through a calcining step in which the virgin support material is heated. The heating reduces the surface area of the support material (e.g. calcining). This provides a method of creating support materials with specific surface areas that may not otherwise be readily available from suppliers.

In another embodiment, it is contemplated to employ at least a plural combination of support materials, each with a different characteristic. For example, at least two support materials (e.g. zirconia) with different characteristics may exhibit different activities and $CO_2$ selectivities, thus permitting preparation of catalysts with a desired set of characteristics, i.e. activity of a catalyst may be balanced against the $CO_2$ selectivity of the catalyst.

In one embodiment, plural different supports are employed in a layered configuration. Layering may be achieved in any of a number of different approaches, such as a plurality of lamella that are generally flat, undulated or a combination thereof. One particular approach is to utilize successively enveloping layers relative to an initial core layer. In general, herein, layered support materials typically include at least an inner layer and an outer layer at least partially surrounding the inner layer. The outer layer preferably contains substantially more of catalytic components than the inner layer. In one embodiment, the inner and outer layers are made of different materials; but the materials may be the same. While the inner layer may be non-porous, other embodiments include an inner layer that is porous.

The layered support material preferably results in a form of a shell catalyst. But the layered support material offers a well defined boundary between the areas of the support material that have catalytic components and the areas that do not. Also, the outer layer can be constructed consistently with a desired thickness. Together the boundary and the uniform thickness of the outer layer result in a shell catalyst that is a shell of catalytic components that is of a uniform and known thickness.

Several techniques are known for creating layered support materials includes those described in U.S. Pat. Nos. 6,486,370; 5,935,889; and 5,200,382, each of which is incorporated by reference. In one embodiment, the materials of the inner layer are also not substantially penetrated by liquids, e.g., metals including but not limited to aluminum, titanium and zirconium. Examples of other materials for the inner layer include, but are not limited to, alumina, silica, silica-alumina, titania, zirconia, niobia, silicates, aluminosilicates, titanates, spinel, silicon carbide, silicon nitride, carbon, cordierite, steatite, bentonite, clays, metals, glasses, quartz, pumice, zeolites, non-zeolitic molecular sieves and combinations thereof. A preferred inner layer is silica and KA160, in particular.

These materials which make up the inner layer may be in a variety of forms such as regularly shaped particulates, irregularly shaped particulates, pellets, discs, rings, stars, wagon wheels, honeycombs or other shaped bodies. A spherical particulate inner layer is preferred. The inner layer, whether spherical or not, has an effective diameter of about 0.02 mm to about 10.0 mm and preferably from about 0.04 mm to about 8.0 mm.

The outermost layer of any multilayer structure is one which is porous, has a surface area in the range of about 5 $m^2/g$ to about 300 $m^2/g$. The material of the outer layer is a metal, ceramic, or a combination thereof, and in one embodiment it is selected from alumina, silica, silica-alumina, titania, zirconia, niobia, silicates, aluminosilicates, titanates, spinel, silicon carbide, silicon nitride, carbon, cordierite, steatite, bentonite, clays, metals, glasses, quartz, pumice, zeolites, non-zeolitic molecular sieves and combinations thereof and preferably include alumina, silica, silica/alumina, zeolites, non-zeolite molecular sieves (NZMS), titania, zirconia and mixtures thereof. Specific examples include zirconia, silica and alumina or combinations thereof.

While the outer layer typically surrounds substantially the entire inner layer, this is not necessarily the case and a selective coating on the inner layer by the outer layer may be employed.

The outer layer may be coated on to the underlying layer in a suitable manner. In one embodiment, a slurry of the outer layer material is employed. Coating of the inner layer with the slurry may be accomplished by methods such as rolling, dipping, spraying, wash coating, other slurry coating techniques, combinations thereof or the like. One preferred technique involves using a fixed or fluidized bed of inner layer particles and spraying the slurry into the bed to coat the particles evenly. The slurry may be applied repeatedly in small amounts, with intervening drying, to provide an outer layer that is highly uniform in thickness.

The slurry utilized to coat the inner layer may also include any of a number of additives such as a surfactant, an organic or inorganic bonding agent that aids in the adhesion of the outer layer to an underlying layer, or combinations thereof. Examples of this organic bonding agent include but are not limited to PVA, hydroxypropylcellulose, methyl cellulose, and carboxymethylcellulose. The amount of organic bonding agent which is added to the slurry may vary, such as from about 1 wt % to about 15 wt % of the combination of outer layer and the bonding agent. Examples of inorganic bonding agents are selected from an alumina bonding agent (e.g. Bohmite), a silica bonding agent (e.g. Ludox, Teos), zirconia bonding agent (e.g. zirconia acetate or colloidal zirconia) or combinations thereof. Examples of silica bonding agents include silica sol and silica gel, while examples of alumina bonding agents include alumina sol, bentonite, Bohmite, and aluminum nitrate. The amount of inorganic bonding agent may range from about 2 wt % to about 15 wt % of the combination of the outer layer and the bonding agent. The thickness of the outer layer may range from about 5 microns to about 500 microns and preferably between about 20 microns and about 250 microns.

Once the inner layer is coated with the outer layer, the resultant layered support will be dried, such as by heating at a temperature of about 100° C. to about 320° C. (e.g. for a time of about 1 to about 24 hours) and then may optionally be calcined at a temperature of about 300° C. to about 900° C. (e.g. for a time of about 0.5 to about 10 hours) to enhance bonding the outer layer to it underlying layer over a least a portion of its surface and provide a layered catalyst support. The drying and calcining steps can be combined into one step. The resultant layered support material may be contacted with catalytic components just as any other support material in the production of catalysts, as described below. Alternately, the outer layer support material is contacted to catalytic components before it is coated onto the underlying layer.

In another embodiment of the layered support, a second outer layer is added to surround the initial outer layer to form at least three layers. The material for the second outer layer may be the same or different than the first outer layer. Suitable materials include those discussed with respect to the first outer layer. The method for applying the second outer layer may be the same or different than the method used to apply the middle layer and suitable methods include those discussed with respect to the first outer layer. Organic or inorganic bonding agents as described may suitably used in the formation of the second outer layer.

The initial outer layer may or may not contain catalytic components. Similarly, the second outer layer may or may not contain catalytic components. If both outer layers contain catalytic component, then preferably different catalytic components are used in each layer, although this is not necessarily the case. In one preferred embodiment, the initial outer layer does not contain a catalytic component. Contacting catalytic component to the outer layers may be accomplished by impregnation or spray coating, as described below.

In embodiments where the initial outer layer contains catalytic component, one method of achieving this is to contact the catalytic component to the material of the initial outer layer before the material is applied to the inner layer. The second outer layer may be applied to the initial outer layer neat or containing catalytic component.

Other suitable techniques may be used to achieve a three layered support material in which one or more of the outer layers contain catalytic components. Indeed, the layered support material is not limited to three layers, but may include four, five or more layers, some or all of which may contain catalytic components.

In addition, the number and type of catalytic components that vary between the layers of the layered support material, other characteristics (e.g. porosity, particle size, surface area, pore volume, or the like) of the support material may vary between the layers.

Methods of Making Catalysts

In general the method includes contacting support material catalytic components and reducing the catalytic components. Preferred methods of the present invention include impregnating the catalytic components into the support material, calcining the catalytic component containing support material, reducing the catalytic components and modifying the reduced catalytic components on the support material. Additional steps such as fixing the catalytic components on the support material and washing the fixed catalytic components may also be included in the method of making the catalyst or pre-catalyst. Some of the steps listed above are optional and others may be eliminated (e.g. the washing and/fixing steps). In addition, some steps may be repeated (e.g. multiple impregnation or fix steps) and the order of the steps may be different from that listed above (e.g. the reducing step precedes the calcining step). To a certain extent, the contacting step will determine what later steps are needed for the formation of the catalyst.

Contacting Step

One particular approach to contacting is one pursuant to which an egg yolk catalyst or pre-catalyst is formed, an egg white catalyst or pre-catalyst is formed, an all throughout catalyst or pre-catalyst is formed or a shell catalyst or pre-catalyst is formed, or a combination thereof. In one embodiment, techniques that form shell catalysts are preferred.

The contacting step may be carried out using any of the support materials described above, with silica, zirconia and layered support materials containing zirconia being the most favored. The contacting step is preferably carried out at ambient temperature and pressure conditions; however, reduced or elevated temperatures or pressures may be employed.

In one preferred contacting step, a support material is impregnated with one or more aqueous solutions of the catalytic components (referred to as precursor solutions). The physical state of the support material during the contacting step may be a dry solid, a slurry, a sol-gel, a colloidal suspension or the like.

In one embodiment, the catalytic components contained in the precursor solution are water soluble salts made of the catalytic components, including but not limited to, chlorides, other halides, nitrates, nitrites, hydroxides, oxides, oxalates, acetates (OAc), and amines, with halide free salts being preferred and chloride free salts being more preferred. Examples of palladium salts suitable for use in precursor solutions include $PdCl_2$, $Na_2PdCl_4$, $Pd(NH_3)_2(NO_2)_2$, $Pd(NH_3)_4(OH)_2$, $Pd(NH_3)_4(NO_3)_2$, $Pd(NO_3)_2$, $Pd(NH_3)_4(OAc)_2$, $Pd(NH_3)_2(OAc)_2$, $Pd(OAc)_2$ in KOH and/or $NMe_4OH$ and/or NaOH, $Pd(NH_3)_4(HCO_3)_2$ and palladium oxalate. Of the chloride-containing palladium precursors, $Na_2PdCl_4$ is most preferred. Of the chloride free palladium precursor salts, the following four are the most preferred: $Pd(NH_3)_4(NO_3)_2$, $Pd(NO_3)_2$, $Pd(NH_3)_2(NO_2)_2$, $Pd(NH_3)_4(OH)_2$. Examples of gold salts suitable for use in precursor solution include $AuCl_3$, $HAuCl_4$, $NaAuCl_4$, $KAuO_2$, $NaAuO_2$, $NMe_4AuO_2$, $Au(OAc)_3$ in KOH and/or $NMe_4OH$ as well as $HAu(NO_3)_4$ in nitric acid, with $KAuO_2$ being the most preferred of the chloride free gold precursors. Examples of rhodium salts suitable for use in precursor solutions include $RhCl_3$, $Rh(OAc)_3$, and $Rh(NO_3)_2$. Similar salts of the above described third catalytic components may also be selected.

Furthermore, more than one salt may be used in a given precursor solution. For example, a palladium salt may be combined with a gold salt or two different palladium salts may be combined together in a single precursor solution. Precursor solutions typically may be made by dissolving the selected salt or salts in water, with or without solubility modifiers such as acids, bases or other solvents. Other non-aqueous solvents may also be suitable.

The precursor solutions may be impregnated onto the support material simultaneously (e.g. co-impregnation) or sequentially and may be impregnated through the use of one or multiple precursor solutions. With three or more catalytic components, a combination of simultaneous and sequential impregnation may be used. For example, palladium and rhodium may be impregnated through the use of a single precursor solution (referred to as a co-impregnation), followed by impregnation with a precursor solution of the gold. In addition, a catalytic component may be impregnated on to support material in multiple steps, such that a portion of the catalytic component is contacted each time. For example, one suitable protocol may include impregnating with Pd, followed by impregnating with Au, followed by impregnating again with Au.

The order of impregnating the support material with the precursor solutions is not critical; although there may be some advantages to certain orders, as discussed below, with respect to the calcining step. Preferably, the palladium catalytic component is impregnated onto the support material first, with gold being impregnated after palladium, or last. Rhodium or other third catalytic component, when used, may be impregnated with the palladium, with the gold or by itself. Also, the support material may be impregnated multiple times with the same catalytic component. For example, a portion of the overall gold contained in the catalyst may be first contacted, followed by contacting of a second portion of the gold. One more other steps may intervene between the steps in which gold is contacted to the support material, e.g. calcining, reducing, and/or fixing.

The acid-base profile of the precursor solutions may influence whether a co-impregnation or a sequential impregnation is utilized. Thus, only precursor solutions with similar acid-base profile should be used together in a co-impregnating step; this eliminates any acid-base reactions that may foul the precursor solutions.

For the impregnating step, the volume of precursor solution is selected so that it corresponds to between about 85% and about 110% of the pore volume of the support material. Volumes between about 95% and about 100% of the pore volume of the support material are preferred, and more preferably between about 98% and about 99% of the pore volume.

Typically, the precursor solution is added to the support material and the support material is allowed absorb the precursor solution. This may be done drop wise until incipient wetness of the support material is substantially achieved. Alternatively, the support material may be placed by aliquots or batch wise into the precursor solution. A roto-immersion or other assistive apparatus may be used to achieve thorough contact between the support material and the precursor solution. Further, a spray device may be used such that the precursor solution is sprayed through a nozzle onto the support material, where it absorbed. Optionally, decanting, heat or reduced pressure may be used to remove any excess liquid not absorbed by the support material or to dry the support material after impregnation.

For the impregnating step, the volume of precursor solution is selected so that it corresponds to between about 85% and about 110% of the pore volume of the support material. Volumes between about 95% and about 100% of the pore volume of the support material are preferred, and more preferably between about 98% and about 99% of the pore volume.

Typically, the precursor solution is added to the support material and the support material is allowed absorb the precursor solution. This may be done drop wise until incipient wetness of the support material is substantially achieved. Alternatively, the support material may be placed by aliquots or batch wise into the precursor solution. A roto-immersion or other assistive apparatus may be used to achieve thorough contact between the support material and the precursor solution. Further, a spray device may be used such that the precursor solution is sprayed through a nozzle onto the support material, where it absorbed. Optionally, decanting, heat or reduced pressure may be used to remove any excess liquid not absorbed by the support material or to dry the support material after impregnation.

Other contacting techniques may be used to avoid a fixing step while still achieving a shell catalyst. For example, catalytic components may be contacted to a support material through a chemical vapor deposition process, such as described in US2001/0048970, which is incorporated by reference. Also, spray coating or otherwise layering a uniformly pre-impregnated support material, as an outer layer, on to an inner layer effectively forms shell catalyst that may also be described as a layered support material. In another technique, organometallic precursors of catalytic components, particularly with respect to gold, may be used to form shell catalysts, as described in U.S. Pat. No. 5,700,753, which is incorporated by reference.

A physical shell formation technique may also be suitable for the production of shell catalysts. Here, the precursor solution may be sprayed onto a heated support material or a layered support material, where the solvent of the precursor solution evaporates upon contact with the heated support material, thus depositing the catalytic components in a shell on the support material. Preferably, temperatures between about 40 and 140° C. may be used. The thickness of the shell may be controlled by selecting the temperature of the support material and the flow rate of the solution through the spray nozzle. For example, with temperatures above about 100° C., a relatively thin shell is formed. This embodiment may be particularly useful when chloride free precursors are utilized to help enhance the shell formation on the support material.

One skilled in the art will understand that a combination of the contacting steps may be an appropriate method of forming a contacted support material.

Fixing Step

It may be desirable to transform at least a portion of the catalytic components on the contacted support material from a water-soluble form to a water-insoluble form. Such a step may be referred to as a fixing step. This may be accomplished by applying a fixing agent (e.g. dispersion in a liquid, such as a solution) to the impregnated support material which causes at least a portion of the catalytic components to precipitate. This fixing step helps to form a shell catalyst, but is not required to form shell catalysts.

Any suitable fixing agent may be used, with hydroxides (e.g. alkali metal hydroxides), silicates, borates, carbonates and bicarbonates in aqueous solutions being preferred. The preferred fixing agent is NaOH. Fixing may be accomplished by adding the fixing agent to the support material before, during or after the precursor solutions are impregnated on the support material. Typically, the fixing agent is used subsequent to the contacting step such that the contacted support material is allowed to soak in the fixing agent solution for about 1 to about 24 hours. The specific time depends upon the combination of the precursor solution and the fixing agent. Like the impregnating step, an assistive device, such as a roto immersion apparatus as described in U.S. Pat. No. 5,332,710, which is incorporated herein by reference, may advantageously be used in the fixing step.

The fixing step may be accomplished in one or multiple steps, referred as a co-fix or a separate fix. In a co-fix, one or more volumes of a fixing agent solution is applied to the contacted support material after all the relevant precursor solutions have been contacted to the support material, whether the contact was accomplished through the use of one or multiple precursor solutions. For example, fixing after sequential impregnation with a palladium precursor solution, a gold precursor solution and a rhodium precursor solution would be a co-fix, as would fixing after a co-impregnation with a palladium/rhodium precursor solution followed by impregnation with a gold precursor solution. An example of co-fixing may be found in U.S. Pat. No. 5,314,888, which is incorporated by reference.

A separate fix, on the other hand, would include applying a fixing agent solution during or after each impregnation with a precursor solution. For example, the following protocols would be a separate fix: a) impregnating palladium followed by fixing followed by impregnating with gold followed by fixing; or b) co-impregnating with palladium and rhodium followed by fixing followed by impregnating with gold followed by fixing. Between a fix and subsequent impregnation, any excess liquid may be removed and the support material dried, although this is not necessarily the case. An example of separate fixing may be found in U.S. Pat. No. 6,034,030, which is incorporated by reference.

In another embodiment, the fixing step and the contacting step are conducted simultaneously, one example of which is described in U.S. Pat. No. 4,048,096, which is incorporated by reference. For example, a simultaneous fix might be: impregnating with palladium followed by fixing followed by impregnating with gold and fixing agent. In a variation on this embodiment, the fix may be conducted twice for a catalytic component. A catalytic component may be partially fixed when it is contacted to the support material (called a "pre-fix"), followed an additional, final fix. For example: impregnating with palladium followed by impregnating with gold and a pre-fixing agent followed by fixing with a final fixing agent. This technique may be used to help insure the formation of shell type catalyst as opposed to an all throughout catalyst.

In another embodiment, particularly suitable for use with chloride free precursors, the support material is pre-treated with a fixing agent to adjust the properties of the support material. In this embodiment, the support material is first impregnated with either an acid or base solution, typically free of metals. After drying, the support material is impregnated with a precursor solution that has the opposite acidity/alkalinity as the dried support material. The ensuing acid-base reaction forms a shell of catalytic components on the support material. For example, nitric acid may be used to pre-treat a support material that in turn is impregnated with a basic precursor solution such as $Pd(OH)_2$ or $Au(OH)_3$. This formation technique may be considered as using a fixing step followed by a contacting step.

The concentration of fixing agent in the solution is typically a molar excess of the amount of catalytic components impregnated on the support material. The amount of fixing agent should be between about 1.0 to about 2.0, preferably about 1.1 to about 1.8 times the amount necessary to react with the catalytically active cations present in the water-soluble salt. In one embodiment using a high Au/Pd atomic or weight ratio, an increased molar excess of hydroxide ion enhances the $CO_2$ selectivity and activity of the resultant catalyst.

The volume of fixing agent solution supplied generally should be an amount sufficient to cover the available free surfaces of the impregnated support material This may be accomplished by introducing, for example, a volume that is greater than the pore volume of the contacted support material.

The combination of impregnating and fixing steps can form a shell type catalyst. But, the use of halide free precursor solutions also permits the formation of a shell catalyst while optionally eliminating the fixing step. In the absence of a chloride precursor, a washing step, as discussed below, may be obviated. Further, the process can be free of a step of fixing catalytic components that would otherwise be needed to survive the washing step. Because no washing step is needed, the catalytic components need not be fixed to survive the washing step. Subsequent steps in the method making the catalyst do not require the catalytic components be fixed and thus the remainder of the step maybe carried out without additional preparatory steps. Overall, the use of chloride free precursors permits a catalyst or pre-catalyst production method that is free of a step of washing, thus reducing the number of steps needed to produce the catalyst and eliminating the need to dispose of chloride containing waste.

Washing Step

Particularly, when halide containing precursor solutions are utilized and in other applications as desired, after the fixing step, the fixed support material may be washed to remove any halide residue on the support or otherwise treated to eliminate the potential negative effect of a contaminant on the support material. The washing step included rinsing the fixed support material in water, preferably deionized water. Washing may be done in a batch or a continuous mode. Washing at room temperature should continue until the effluent wash water has a halide ion content of less than about 1000 ppm, and more preferably until the final effluent gives a negative result to a silver nitrate test. The washing step may be carried out after or simultaneously with the reducing step, discussed below, but preferably is carried out before. As discussed above, the use of halide free precursor solutions permits the elimination of the washing step.

Calcining Step

After at least one catalytic component has been contacted to the support material, a calcining step may be employed. The calcining step typically is before the reducing step and after the fixing step (if such a step is used) but may take place elsewhere in the process. In another embodiment, the calcining step is carried out after the reducing step. The calcining step includes heating the support material in a non-reducing atmosphere (i.e. oxidizing or inert). During calcination, the catalytic components on the support material are at least partially decomposed from their salts to a mixture of their oxide and free metal form.

For example, the calcining step is carried out at a temperature in the range of about 100° C. to about 700° C., preferably between about 200° C. and about 500° C. Non-reducing gases used for the calcination may included one or more inert or oxidizing gases such as helium, nitrogen, argon, neon, nitrogen oxides, oxygen, air, carbon dioxide, combinations thereof or the like. In one embodiment, the calcining step is carried out in an atmosphere of substantially pure nitrogen, oxygen, air or combinations thereof. Calcination times may vary but preferably are between about 1 and 5 hours. The degree of decomposition of the catalytic component salts depends on the temperature used and length of time the impregnated catalyst is calcined and can be followed by monitoring volatile decomposition products.

One or more calcining steps may be used, such that at any point after at least one catalytic component is contacted to the support material, it may be calcined. Preferably, the last calcining step occurs before contact of the gold catalytic component to a zirconia support material. Alternately, calcining of a zirconia support material containing gold is conducted at temperatures below about 300° C. By avoiding calcining the gold containing zirconia support material at temperatures above about 300° C., the risk that the $CO_2$ selectivity of the resultant catalyst will be detrimentally affected is reduced.

Exemplary protocols including a calcining step include: a) impregnating with palladium followed by calcining followed by impregnating with gold; b) co-impregnating palladium and rhodium followed by calcining followed by impregnating with Au; c) impregnating with palladium followed by calcining followed by impregnating with rhodium followed by calcining followed by impregnating with gold; or d) impregnating with palladium and rhodium, followed by impregnating with gold, followed by calcination.

Reducing Step

Another step employed generally herein to at least partially transform any remaining catalytic components from a salt or oxide form to a catalytically active state, such as by a reducing step. Typically this is done by exposure of salts or oxides to a reducing agent, examples of which include ammonia, carbon monoxide, hydrogen, hydrocarbons, olefins, aldehydes, alcohols, hydrazine, primary amines, carboxylic acids, carboxylic acid salts, carboxylic acid esters and combinations thereof. Hydrogen, ethylene, propylene, alkaline hydrazine and alkaline formaldehyde and combinations thereof are preferred reducing agents with ethylene and hydrogen blended with inert gases particularly preferred. Although reduction employing a gaseous environment is preferred, a reducing step carried with a liquid environment may also be used (e.g. employing a reducing solution). The temperature selected for the reduction can range from ambient up to about 550° C. Reduction times will typically vary from about 1 to about 5 hours.

Since the process used to reduce the catalytic components may influences the characteristics of the final catalyst, conditions employed for the reduction may be varied depending on whether high activity, high selectivity or some balance of these properties is desired.

In one embodiment, palladium is contacted to the support material, fixed and reduced before gold is contacted and reduced, as described in U.S. Pat. Nos. 6,486,093, 6,015,769 and related patents, all of which are incorporated by reference.

Exemplary protocols including a reducing step include: a) impregnating with palladium followed by optionally calcining followed by impregnating with gold followed by reducing; b) co-impregnating with palladium and gold followed by optionally calcining followed by reducing; or c) impregnating with palladium followed by optionally calcining followed by reducing followed by impregnating with gold.

Modifying Step

Usually after the reducing step and before the catalyst is used, a modifying step is desirable. While the catalyst may be used with the modifying step, the step has several beneficial results, including lengthening the operational life time of the catalyst. The modifying step is sometimes called an activating step and may be accomplished in accordance with conventional practice. Namely, the reduced support material is contacted with a modifying agent, such as an alkali metal carboxylate and/or alkali metal hydroxide, prior to use. Conventional alkali metal carboxylates such as the sodium, potassium, lithium and cesium salts of $C_{2-4}$ aliphatic carboxylic acids are employed for this purpose. A preferred activating agent in the production of VA is an alkali acetate, with potassium acetate (KOAc) being the most preferred.

The support material may optionally be impregnated with a solution of the modifying agent. After drying, the catalyst may contain, for example, about 10 to about 70, preferably about 20 to about 60 grams of modifying agent per liter of catalyst.

Methods of Making Alkenyl Alkanoates

The present invention may be utilized to produce alkenyl alkanoates from an alkene, alkanoic acid and an oxygen containing gas in the presence of a catalyst. Preferred alkene starting materials contain from two to four carbon atoms (e.g. ethylene, propylene and n-butene). Preferred alkanoic acid starting materials used in the process of this invention for producing alkenyl alkanoates contain from two to four carbon atoms (e.g., acetic, propionic and butyric acid). Preferred products of the process are VA, vinyl propionate, vinyl butyrate, and allyl acetate. The most preferred starting materials are ethylene and acetic acid with the VA being the most preferred product. Thus, the present invention is useful in the production of olefinically unsaturated carboxylic esters from an olefinically unsaturated compound, a carboxylic acid and oxygen in the presence of a catalyst. Although the rest of the specification discusses VA exclusively, it should be understood that the catalysts, method of making the catalysts and production methods are equally applicable to other alkenyl alkanoates, and the description is not intended as limiting the application of the invention to VA.

When VA is produced using the catalyst of the present invention, a stream of gas, which contains ethylene, oxygen or air, and acetic acid is passed over the catalyst. The composition of the gas stream can be varied within wide limits, taking in account the zone of flammability of the effluent. For example, the molar ratio of ethylene to oxygen can be about 80:20 to about 98:2, the molar ratio of acetic acid to ethylene can be about 100:1 to about 1:100, preferably about 10:1 to 1:10, and most preferably about 1:1 to about 1:8. The gas stream may also contain gaseous alkali metal acetate and/or inert gases, such as nitrogen, carbon dioxide and/or saturated hydrocarbons. Reaction temperatures which can be used are elevated temperatures, preferably those in the range of about 125-220° C. The pressure employed can be a somewhat reduced pressure, normal pressure or elevated pressure, preferably a pressure of up to about 20 atmospheres gauge.

In addition to fixed bed reactors, the methods of producing alkenyl alkanoates and the catalyst of the present invention may also be suitably employed in other types of reaction, for example, fluidized bed reactors.

EXAMPLES

The following examples are provided for illustration only and not intended to be limiting. The amounts solvents and reactants are approximate. The Au/Pd atomic ratio may be converted to the Au/Pd weight ratio and vice versa by the following equations: Au/Pd atomic ratio=0.54*(Au/Pd weight ratio) and Au/Pd weight ratio=1.85(Au/Pd atomic ratio. Reduction may be abbreviated 'R' followed by the temperature in ° C. at which the reduction was carried out. Likewise, calcination may be abbreviated 'C' followed by the temperature in ° C. at which the calcination was carried out, whereas a drying step may be abbreviated as 'dry'.

The catalyst of examples 1-11 may be prepared as described in the example and tested according to the following procedure, where catalyst from Examples 1-7 may be compared to each other and catalyst from 8-11 may be compared to each other. Results are provided where available.

The catalysts of the examples were tested for their activity and selectivity to various by-products in the production of vinyl acetate by reaction of ethylene, oxygen and acetic acid. To accomplish this, about 60 ml of the catalyst prepared as described were placed in a stainless steel basket with the temperature capable of being measured by a thermocouple at both the top and bottom of the basket. The basket was placed in a Berty continuously stirred tank reactor of the recirculating type and was maintained at a temperature which provided about 45% oxygen conversion with an electric heating mantle. A gas mixture of about 50 normal liters (measured at N.T.P.) of ethylene, about 10 normal liters of oxygen, about 49 normal liters of nitrogen, about 50 g of acetic acid, and about 4 mg of potassium acetate, was caused to travel under pressure at about 12 atmospheres through the basket, and the catalyst was aged under these reaction conditions for at least 16 hours prior to a two hour run, after which the reaction was terminated. Analysis of the products was accomplished by on-line gas chromatographic analysis combined with off-line liquid product analysis by condensing the product stream at about 10° C. to obtain optimum analysis of the end products carbon dioxide ($CO_2$), heavy ends (HE) and ethyl acetate (EtOAc), the results of which may be used to calculate the percent selectivities ($CO_2$ Selectivity) of these materials for each example. The relative activity of the reaction expressed as an activity factor (Activity) may be computer calculated using a series of equations that correlates the activity factor with the catalyst temperature (during the reaction), oxygen conversion, and a series of kinetic parameters for the reactions that take place during VA synthesis. More generally, the activity factor typically is inversely related to the temperature required to achieve constant oxygen conversion.

Rhodium Catalyst Examples

Example 1

A support material containing palladium and rhodium metal was prepared as follows: The support material in an amount of 250 ml consisting of Sud Chemie KA-160 silica spheres having a nominal diameter of 7 mm., a density of about 0.569 g/ml, in absorptivity of about 0.568 g $H_2O$/g support, a surface area of about 160 to 175 $m^2$/g, and a pore volume of about 0.68 ml/g., was first impregnated by incipient wetness with 82.5 ml of an aqueous solution of sodium tetrachloropalladium (II) ($Na_2PdCl_4$) and rhodium chloride trihydrite ($RhCl_3 \cdot 3H2O$) sufficient to provide about 7 grams of elemental palladium and about 0.29 grams of elemental rhodium per liter of catalyst. The support was shaken in the solution for 5 minutes to ensure complete absorption of the solution. The palladium and rhodium were then fixed to the support as palladium (II) and rhodium (III) hydroxides by contacting the treated support by roto-immersion for 2.5 hours at approximately 5 rpm with 283 ml of an aqueous sodium hydroxide solution prepared from 50% w/w NaOH/$H_2O$ in an amount of 120% of that needed to convert the palladium and rhodium to their hydroxides. The solution was drained from the treated support and the support was then rinsed with deionized water and dried at 100° C. in a fluid bed drier for 1.2 hours. The support material containing palladium and rhodium hydroxides was then impregnated with an aqueous solution (81 ml) containing 1.24 g Au from $NaAuCl_4$ and 2.71 g 50% NaOH solution (1.8 equivalents with respect to Au) using the incipient wetness method. The NaOH treated pills were allowed to stand overnight to ensure precipitation of the Au salt to the insoluble hydroxide. The pills were thoroughly washed with deionized water (~5 hours) to remove chloride ions and subsequently dried at 100° C. in a fluid bed drier for 1.2 hours. The palladium, rhodium, and gold containing support was then calcined at 400° C. for 2 hours under air and then allowed to naturally cool to room temperature. The palladium, rhodium, and gold were reduced by contacting the support with $C_2H_4$ (1% in nitrogen) in the vapor phase at 150° C. for 5 hours. Finally the catalyst was impregnated by incipient wetness with an aqueous solution of 10 g of potassium acetate in 81 ml $H_2O$ and dried in a fluid bed drier at 100° C. for 1.2 hours.

Example 2

A support material utilizing palladium and rhodium hydroxides was prepared as described in Example 1. The palladium and rhodium containing support was then calcined at 400° C. for 2 hours under air and then allowed to naturally cool to room temperature. The calcined support material containing palladium and rhodium hydroxides was then impregnated with an aqueous solution (81 ml) containing 1.24 g Au from $NaAuCl_4$ and 2.71 g 50% NaOH solution (1.8 equivalents with respect to Au) using the incipient wetness method.

The NaOH treated pills were allowed to stand overnight to ensure precipitation of the Au salt to the insoluble hydroxide. The pills were thoroughly washed with deionized water (~5 hours) to remove chloride ions and subsequently dried at 100° C. in a fluid bed drier for 1.2 hours. The palladium, rhodium, and gold were then reduced by contacting the support with $C_2H_4$ (1% in nitrogen) in the vapor phase at 150° C. for 5 hours. Finally the catalyst was impregnated by incipient wetness with an aqueous solution of 10 g of potassium acetate in 81 ml $H_2O$ and dried in a fluid bed drier at 100° C. for 1.2 hours.

Example 3

A support material containing palladium and rhodium hydroxides was prepared as described in Example 1. The palladium and rhodium containing support was then calcined at 400° C. for 2 hours under air and then allowed to naturally cool to room temperature. The calcined support material containing palladium and rhodium hydroxides was then reduced by contacting the support with $C_2H_4$ (1% in nitrogen) in the vapor phase at 150° C. for 5 hours. The support containing palladium and rhodium metal was subsequently impregnated with an aqueous solution (81 ml) containing 1.24 g Au from $NaAuCl_4$ and 2.71 g 50% NaOH solution (1.8 equivalents with respect to Au) using the incipient wetness method. The NaOH treated pills were allowed to stand overnight to ensure precipitation of the Au salt to the insoluble hydroxide. The pills were thoroughly washed with deionized water (~5 hours) to remove chloride ions and subsequently dried at 100° C. in a fluid bed drier for 1.2 hours. The palladium, rhodium, and gold were then reduced by contacting the support with $C_2H_4$ (1% in nitrogen) in the vapor phase at 150° C. for 5 hours. Finally the catalyst was impregnated by incipient wetness with an aqueous solution of 10 g of potassium acetate in 81 ml $H_2O$ and dried in a fluid bed drier at 100° C. for 1.2 hours.

Example 4

A support material containing palladium and rhodium hydroxides was prepared as described in Example 1. The palladium and rhodium containing support was then calcined at 400° C. for 2 hours under air and then allowed to naturally cool to room temperature. The calcined support material containing palladium and rhodium hydroxides was then reduced by contacting the support with $C_2H_4$ (1% in nitrogen) in the vapor phase at 150° C. for 5 hours. The support containing palladium and rhodium metal was subsequently impregnated with an aqueous solution (81 ml) containing 1.1 g Au from $KAuO_2$ using the incipient wetness method. The pills were subsequently dried at 100° C. in a fluid bed drier for 1.2 hours. The palladium, rhodium, and gold were then reduced by contacting the support with $C_2H_4$ (1% in nitrogen) in the vapor phase at 150° C. for 5 hours. Finally the catalyst was impregnated by incipient wetness with an aqueous solution of 10 g of potassium acetate in 81 ml $H_2O$ and dried in a fluid bed drier at 100° C. for 1.2 hours.

Example 5

A support material containing palladium and rhodium hydroxides was prepared as described in Example 1. The palladium and rhodium containing support was then calcined at 400° C. for 2 hours under air and then allowed to naturally cool to room temperature. The calcined support containing palladium and rhodium hydroxides was subsequently impregnated with an aqueous solution (81 ml) containing 1.1 g Au from $KAuO_2$ using the incipient wetness method. The pills were then dried at 100° C. in a fluid bed drier for 1.2 hours. The palladium, rhodium, and gold were then reduced by contacting the support with $C_2H_4$ (1% in nitrogen) in the vapor phase at 150° C. for 5 hours. Finally the catalyst was impregnated by incipient wetness with an aqueous solution of 10 g of potassium acetate in 81 ml $H_2O$ and dried in a fluid bed drier at 100° C. for 1.2 hours.

Example 6

A support material containing palladium and rhodium hydroxides was prepared as described in Example 1. The palladium and rhodium containing support was then calcined at 400° C. for 2 hours under air and then allowed to naturally cool to room temperature. The calcined support material containing palladium and rhodium hydroxides was then reduced by contacting the support with $C_2H_4$ (1% in nitrogen) in the vapor phase at 150° C. for 5 hours. The support containing palladium and rhodium metal was subsequently impregnated with an aqueous solution (81 ml) containing 1.1 g Au from $KAuO_2$ and 10 g potassium acetate using the incipient wetness method. The pills were subsequently dried at 100° C. in a fluid bed drier for 1.2 hours.

Example 7

Reference Catalyst

A support material containing palladium metal was prepared as follows: The support material in an amount of 250 ml consisting of Sud Chemie KA-160 silica spheres having a nominal diameter of 7 mm., a density of about 0.569 g/ml, in absorptivity of about 0.568 g $H_2O$/g support, a surface area of about 160 to 175 $m^2$/g, and a pore volume of about 0.68 ml/g., was first impregnated by incipient wetness with 82.5 ml of an aqueous solution of sodium tetrachloropalladium (II) ($Na_2PdCl_4$) sufficient to provide about 7 grams of elemental palladium per liter of catalyst. The support was shaken in the solution for 5 minutes to ensure complete absorption of the solution. The palladium was then fixed to the support as palladium (II) hydroxides by contacting the treated support by roto-immersion for 2.5 hours at approximately 5 rpm with 283 ml of an aqueous sodium hydroxide solution prepared from 50% w/w NaOH/$H_2O$ in an amount of 110% of that needed to convert the palladium to its hydroxide. The solution was drained from the treated support and the support was then rinsed with deionized water and dried at 100° C. in a fluid bed drier for 1.2 hours. The support material containing palladium hydroxide was then impregnated with an aqueous solution (81 ml) containing 1.24 g Au from $NaAuCl_4$ and 2.71 g 50% NaOH solution (1.8 equivalents with respect to Au) using the incipient wetness method. The NaOH treated pills were allowed to stand overnight to ensure precipitation of the Au salt to the insoluble hydroxide. The pills were thoroughly washed with deionized water (~5 hours) to remove chloride ions and subsequently dried at 100° C. in a fluid bed drier for 1.2 hours. The palladium and gold containing support was then reduced by contacting the support with $C_2H_4$ (1% in nitrogen) in the vapor phase at 150° C. for 5 hours. Finally the catalyst was impregnated by incipient wetness with an aqueous solution of 10 g of potassium acetate in 81 ml $H_2O$ and dried in a fluid bed drier at 100° C. for 1.2 hours. Table 1 shows comparison $CO_2$ selectivity and activity for the catalyst of Examples 1 and 7.

TABLE 1

|  | $CO_2$ Selectivity | Activity |
|---|---|---|
| Example 1 | 9.89 | 2.32 |
| Example 7 (Reference Catalyst) | 11.13 | 2.36 |

Layered Support Examples

Example 8

40 g of $ZrO_2$ (RC-100, supplied by DKK) was calcined at 650° C. for 3 h. Resulting material has a BET surface area 38 m²/g. The material was ball milled with 120 ml of DI water for 6 h. The sol was mixed with 22.5 g of the binder zirconium acetate supplied by DKK (ZA-20) and sprayed onto 55 g of spheres of bentonite KA-160 with OD~7.5 mm. Coated beads were calcined for 3 h at 600° C. Examination under microscope has shown uniform shell formation with thickness of 250 μm.

Example 9

20 g of $ZrO_2$ (XZ16075, BET surface area 55 m²/g) were impregnated with $Pd(NO_3)_2$ solution (Aldrich) to give Pd loading of 39 mg/g of ZrO2. Impregnated material was dried and calcined at 450° C. for 4 h. The material was ball milled with 60 ml of DI water for 4 h, mixed with 11 g of a binder (ZA-20) and sprayed onto 30 g of bentonite KA-160 spheres. The beads were calcined at 450° C. for 3 h. This procedure results in formation of a strong uniform shell with 160 μm thickness.

Example 10

The beads from Example 8 were impregnated with solution of potassium acetate to give loading of 40 mg KOAc/ml of KA-160, dried and calcined at 300° C. for 4 h. After that the solution, containing 9.4 mM of Pd (from $Pd(NH_3)_4(OH)_2$ supplied by Heraeus) and 4.7 mM of Au (from a 1 M solution, $Au(OH)_3$ "Alfa" dissolved in 1.6 M KOH) was sprayed onto these beads. Material was reduced with the mixture: 5% $H_2$, 95% $N_2$ at 200° C. for 4 h. The beads were crushed and tested in fix bed micro reactor under conditions described in the experimental section. $CO_2$ selectivity of ~6% at 45% oxygen conversion was achieved.

Example 11

Reference Catalyst

The same catalyst prepared in Example 7 was used as a reference catalyst here. Table 2 shows comparison $CO_2$ selectivity and activity for the catalyst of Examples 9-11.

TABLE 2

|  | $CO_2$ Selectivity | Activity |
|---|---|---|
| Example 9 | 9.33 | 2.08 |
| Example 10 | 9.03 | 1.69 |
| Example 11 (Reference Catalyst) | 11.13 | 2.36 |

Zirconia Support Material and Chloride Free Precursor Examples

The following general procedure was used for this set of examples. Zirconia support material catalysts were made as follows: various shaped catalyst carriers were crushed and sieved. Zirconia support materials were supplied by N or Pro (XZ16052 and XZ16075), DKK and MEI. Silica support materials were supplied by Degussa and Sud Chemie. The sieve fraction of 180-425 um was impregnated (either simultaneously or sequentially with an intermediate drying step at 110° C. and optionally with an intermediate calcination step) to incipient wetness with a Pd and Au precursor solution, optionally calcined in air, reduced with 5% $H_2/N_2$ formation gas, post-impregnated with KOAc solution, dried at 100° C. under $N_2$, and screened in a 8×6 multi channel fixed bed reactor. A solution of $Au(OH)_3$ in KOH was used as the Au precursor. Aqueous solutions of $Pd(NH_3)_4(OH)_2$, $Pd(NH_3)_2(NO_2)_2$, $Pd(NH_3)_4(NO_3)_2$ and $Pd(NO_3)_2$ were used as the Pd precursors.

A silica support material catalyst reference was made as follows: A support material containing palladium and rhodium metal was prepared as follows: The support material in an amount of 250 ml consisting of Sud Chemie KA-160 silica spheres having a nominal diameter of 7 mm, a density of about 0.569 g/ml, an absorptivity of about 0.568 g $H_2O$/g support, a surface area of about 160 to 175 m²/g, and a pore volume of about 0.68 ml/g., was first impregnated by incipient wetness with 82.5 ml of an aqueous solution of sodium tetrachloropalladium (II) ($Na_2PdCl_4$) sufficient to provide about 7 grams of elemental palladium per liter of catalyst. The support was shaken in the solution for 5 minutes to ensure complete absorption of the solution. The palladium was then fixed to the support as palladium(II) hydroxides by contacting the treated support by roto-immersion for 2.5 hours at approximately 5 rpm with 283 ml of an aqueous sodium hydroxide solution prepared from 50% w/w $NaOH/H_2O$ in an amount of 110% of that needed to convert the palladium to its hydroxide. The solution was drained from the treated support and the support was then rinsed with deionized water and dried at 100° C. in a fluid bed drier for 1.2 hours. The support material containing palladium hydroxide was then impregnated with an aqueous solution (81 ml) containing 1.24 g Au from $NaAuCl_4$ and 2.71 g 50% NaOH solution (1.8 equivalents with respect to Au) using the incipient wetness method. The NaOH treated pills were allowed to stand overnight to ensure precipitation of the Au salt to the insoluble hydroxide. The pills were thoroughly washed with deionized water (~5 hours) to remove chloride ions and subsequently dried at 100° C. in a fluid bed drier for 1.2 hours. The palladium and gold containing support was then reduced by contacting the support with $C_2H_4$ (1% in nitrogen) in the vapor phase at 150° C. for 5 hours. Finally the catalyst was impregnated by incipient wetness with an aqueous solution of 10 g of potassium acetate in 81 ml $H_2O$ and dried in a fluid bed drier at 100° C. for 1.2 hours. Before testing, the catalyst was crushed and sieved. The sieved fraction in the size range of 180-425 um was used.

Catalyst libraries of arrays of 8 rows×6 columns in glass vials were designed and a rack of 36 glass vials was mounted on a vortexer and agitated while dispensing metal precursor solutions using Cavro™ liquid dispensing robots. 0.4 ml of support was used for each library element, for the glass vial synthesis as well as loaded to each reactor vessel.

KOAc loading is reported as grams KOAc per liter catalyst volume or as μmol KOAc on 0.4 ml support. For the specification of Au loading, the relative atomic ratio of Au to Pd is reported as Au/Pd. Pd loading is specified as mg Pd per 0.4 ml support volume (i.e. absolute amount of Pd in reactor vessel).

The screening protocol used a temperature ramp from 145° C. to 165° C. in 5° C. increments, at a fixed space velocity of 175% (with 1.5 mg Pd on 0.4 ml support). 100% space velocity is defined as the following flows: 5.75 sccm of Nitrogen, 0.94 sccm of Oxygen, 5.94 sccm of Ethylene, and 5.38 microliters per minute of Acetic Acid through each of the 48 catalyst vessels (all of which had an inner diameter of approximately 4 mm). $CO_2$ selectivity was plotted versus oxygen conversion, a linear fit performed, and the calculated (interpolated in most cases) $CO_2$ selectivity at 45% oxygen conversion reported in the performance summary tables below. The temperature at 45% oxygen conversion calculated from the T ramp (linear fits of $CO_2$ selectivity and oxygen conversion versus reaction temperature is also reported). The lower this calculated temperature the higher the activity of the catalyst. The space time yield (STY; g VA produced per ml catalyst volume per h) at 45% oxygen conversion is a measure of the productivity of the catalyst.

Example 12

400 ul of $ZrO_2$ carriers XZ16075 (55 $m^2$/g as supplied) and XZ16052 (precalcined at 650° C./2 h to lower the surface area to 42 $m^2$/g) were impregnated with 3 different Pd solutions to incipient wetness, dried at 110° C. for 5 h, impregnated with $KAuO_2$ (0.97M Au stock solution) to incipient wetness, dried at 110° C. for 5 h, reduced at 350° C. for 4 h in 5% $H_2/N_2$ formation gas, post-impregnated with KOAc and dried at 110° C. for 5 h. The Pd/Au/$ZrO_2$ samples (shells) were then diluted 1/9.3 with KA160 diluter (preloaded with 40 g/l KOAc), i.e. 43 ul Pd/Au/$ZrO_2$ shell and 357 ul diluter (400 ul total fixed bed volume) were charged to the reactor vessels. The Pd loading was 14 mg Pd in 400 ul ZrO2 shell (or 14*43/400=14/9.3=1.5 mg Pd in reactor vessel for all library elements. The Pd precursors were $Pd(NH_3)_2(NO_2)_2$ in columns 1 and 4, $Pd(NH_3)_4(OH)_2$ in columns 2 and 5, $Pd(NH_3)_4(NO_3)_2$ in columns 3 and 6. Au/Pd=0.3 in row 2 and row 5, Au/Pd=0.6 in row 3, Au/Pd=0.9 in row 4, row 6 and row 7. The KOAc loading was 114 umol in rows 2, 3, 5 and 147 umol in rows 4, 6, 7. The silica reference catalyst was loaded into Row 1. The library was screened using the T ramp screening protocol at fixed SV. Screening results are summarized in Table 3

TABLE 3

| | $CO_2$ Selectivity | Temp at | STY |
|---|---|---|---|
| Cl Precursors on $SiO_2$ | 7.37 | 156.6 | 729 |
| $Pd(NH_4)_2(OH)_2$ on $ZrO_2$ | 5.79 | 152.4 | 787 |
| $Pd(NH_3)_4(NO_3)_2$ on $ZrO_2$ | 5.90 | 152.3 | 783 |
| $Pd(NH_3)_2(NO_2)_2$ on $ZrO_2$ | 5.57 | 150.7 | 795 |

*Data shown is taken from average of two Au/Pd atomic ratios (namely 0.3 and 0.6) and two different $ZrO_2$ supports.

Example 13

400 ul of $ZrO_2$ carriers XZ16075 (55 $m^2$/g as supplied) and XZ16052 (precalcined at 650° C./2 h to lower the surface area to 42 $m^2$/g) were impregnated with $Pd(NH_3)_4(OH)_2$ (1.117M Pd stock solution) to incipient wetness, calcined at 350° C. for 4 h in air, impregnated with $KAuO_2$ (0.97M Au stock solution) to incipient wetness, dried at 110° C. for 5 h, reduced at 350° C. for 4 h in 5% $H_2/N_2$ formation gas, post-impregnated with KOAc and dried at 110° C. for 5 h. The Pd/Au/$ZrO_2$ samples (shells) were then diluted 1/12 with KA160 diluter (preloaded with 40 g/l KOAc), i.e. 33.3 ul Pd/Au/$ZrO_2$ catalyst and 366.7 ul diluter (400 ul total fixed bed volume) were charged to the reactor vessels. The library design and library element compositions were as follows: $ZrO_2$ XZ16075 in columns 1-3 (left half of library) and ZrO2 XZ16052 (650° C.) in columns 4-6 (right half of library). The Pd loading was 18 mg Pd in 400 ul $ZrO_2$ shell (or 18*33/400=18/12 mg Pd in reactor vessel) in cell G2, column 3 (cells B3-G3), cell G5, column 6 (cells B6-G6); 10 mg Pd in 400 ul $ZrO_2$ shell (or 10*33/400=10/12 mg Pd in reactor vessel) in column 1 (cells A1-G1) and column 4 (cells A4-G4); 14 mg Pd in 400 ul $ZrO_2$ shell (or 14*33/400=14/12 mg Pd in reactor vessel) in column 2 (cells B2-F2) and column 5 (cells B5-F5). Au/Pd=0.3 in row 2 and row 5, Au/Pd=0.5 in row 3 and row 6, Au/Pd=0.7 in row 4 and row 7 (except cells A1, A4, G2, G5 where Au/Pd was 0.3). The KOAc loading was 114 umol (except cells D3, G3, D6, G6 where KOAc loading was 147 umol). The silica reference catalyst was loaded into Row 1. The library was screened using the T ramp screening protocol at fixed SV. Screening results are summarized in Table 4.

TABLE 4

| | $CO_2$ Selectivity | | | Temp at 45% Conv | | | STY | | |
|---|---|---|---|---|---|---|---|---|---|
| Au/Pd Atomic Ratio | 0.3 | 0.5 | 0.7 | 0.3 | 0.5 | 0.7 | 0.3 | 0.5 | 0.7 |
| Cl Precursors on $SiO_2$ | 6.98 | — | — | 154.8 | — | — | 742.8 | — | — |
| $ZrO_2$: XZ16052 | 6.06 | 5.31 | 5.38 | 153.7 | 152.3 | 154.9 | 776.8 | 806.0 | 803.0 |
| $ZrO_2$: XZ16075 | 6.18 | 5.62 | 5.71 | 147.5 | 151.0 | 154.4 | 773.8 | 791.6 | 790.3 |

Example 14

ZrO2 carrier (supplied by N or Pro, XZ16075, sieve fraction 180-425 um, density 1.15 g/ml, pore volume 475 ul/g, BET surface area 55 m2/g) was impregnated with $Pd(NO3)_2$ precursor solution to incipient wetness, dried at 110° C., calcined at 250° C. (columns 1-2), 350° C. (columns 3-4), 450° C. (columns 5-6) in air, impregnated with $KAuO_2$ solution (prepared by dissolution of $Au(OH)_3$ in KOH), dried at 110° C., reduced with 5% $H_2/N_2$ formation gas at 350° C. for 4 h, and post-impregnated with KOAc solution. The library has a KOAc gradient from 25 to 50 µl in row 2 to row 7. The Pd loading amounts to 1.5 mg Pd on 0.4 ml support. Two different Au loadings were chosen (Au/Pd=0.5 in columns 1, 3, 5 and Au/Pd=0.7 in columns 2, 4, 6). The silica reference catalyst was loaded in row 1. The library was screened using the T ramp screening protocol in MCFB48 VA reactor at fixed SV. Screening results are summarized in Table 5.

TABLE 5

| | $CO_2$ Selectivity | Temp at 45% Conv | STY |
|---|---|---|---|
| Cl Precursors on $SiO_2$ | 7.21 | 154.7 | 734 |
| Pd(NO3)2 on ZrO2 | 6.10 | 145.3 | 775 |

*Data shown is taken from average of two Au/Pd atomic ratios (namely 0.5 and 0.7) at 40 g/L KOAc, calcination at 450° C., and reduction at 350° C.

Example 15

ZrO$_2$ carrier (supplied by N or Pro, XZ16075, sieve fraction 180-425 um, density 1.15 g/ml, pore volume 575 ul/g, BET surface area 55 m2/g) was impregnated with Pd(NO3)$_2$ precursor solution to incipient wetness, dried at 110° C., calcined at 450° C. in air, impregnated with KAuO$_2$ solution (prepared by dissolution of Au(OH)$_3$ in KOH), dried at 110° C., reduced with 5% H$_2$/N$_2$ formation gas at 200° C. (columns 1-2), 300° C. (columns 3-4), or 400° C. (columns 5-6), and post-impregnated with KOAc solution. The library has a KOAc gradient from 15 to 40 g/l in row 2 to row 7. The Pd loading amounts to 1.5 mg Pd on 0.4 ml support. Two different Au loadings were chosen (Au/Pd=0.5 in columns 1, 3, 5 and Au/Pd=0.7 in columns 2, 4, 6). The silica reference catalyst was loaded in row 1. The library was screened in MCFB48 VA reactor using the T ramp screening protocol at fixed SV. Screening results are summarized in Table 6.

TABLE 6

|  | CO$_2$ Selectivity | Temp at 45% Conv | STY |
|---|---|---|---|
| Cl Precursors on SiO$_2$ | 7.11 | 154.2 | 738 |
| Pd(NO3)2 on ZrO2 | 5.51 | 145.4 | 797 |

*Data shown is taken from average of two Au/Pd atomic ratios (namely 0.5 and 0.7) at 40 g/L KOAc, calcination at 450° C., and reduction at 400° C.

It will be further appreciated that functions or structures of a plurality of components or steps may be combined into a single component or step, or the functions or structures of one step or component may be split among plural steps or components. The present invention contemplates all of these combinations. Unless stated otherwise, dimensions and geometries of the various structures depicted herein are not intended to be restrictive of the invention, and other dimensions or geometries are possible. Plural structural components or steps can be provided by a single integrated structure or step. Alternatively, a single integrated structure or step might be divided into separate plural components or steps. In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes.

We claim:

1. A method of producing a catalyst or pre-catalyst suitable for assisting in the production of alkenyl alkanoates, comprising:
   impregnating palladium, gold and rhodium precursors on to a support material;
   calcining the contacted support material in a non-reducing atmosphere; and
   reducing the palladium and rhodium precursors by contacting a reducing environment to the support material; and
   contacting an alkali metal acetate to the reduced support material to form an alkenyl alkanoates catalyst or pre-catalyst.

2. The method of claim 1 wherein the impregnating step comprises co-impregnating palladium and rhodium precursors, followed by impregnating with the gold precursor.

3. The method of claim 1 wherein the impregnating step comprises co-impregnating palladium, rhodium and gold precursors.

4. The method of claim 1 further comprising at least one fixing step of fixing at least one of the precursors with a fixing agent.

5. The method of claim 1 wherein the calcining step comprises heating the contacted support material at a temperature between about 200° C. and about 700° C.

6. The method of claim 1 wherein the impregnating step comprises impregnating the support material with at least one substantially chloride-free water soluble precursor of palladium, rhodium or gold.

7. The method of claim 1 wherein the support material comprises silica.

8. The method of claim 1 wherein the support material comprises silica and alumina.

9. The method of claim 1 wherein the support material comprises zirconia.

10. The method of claim 1 wherein the support material comprises a layered support material.

11. The method of claim 1 wherein the alkali metal acetate is potassium acetate.

12. The method of claim 1 wherein the alkali metal acetate is present in an amount of between about 10 and 70 grams per liter of catalyst.

13. The method of claim 1 wherein the contacting step comprises contacting between about 1 to about 10 grams of palladium, and about 0.5 to about 10 grams of gold per liter of catalyst, with the amount of gold being from about 10 to about 125 wt % based on the weight of palladium.

14. A composition for catalyzing the production of an alkenyl alkanoates, comprising:
   a support material with at least palladium, rhodium, and gold and an alkali metal acetate contacted thereon to form an alkenyl alkanoates catalyst or pre-catalyst, wherein at least palladium and rhodium have been calcined in a non-reducing atmosphere.

15. The composition of claim 14 wherein the support material comprises silica.

16. The composition of claim 14 wherein the support material comprises silica and alumina.

17. The composition of claim 14 wherein the support material comprises zirconia.

18. The composition of claim 14 wherein the support material comprises a layered support material.

19. The composition of claim 14 wherein the catalyst or pre-catalyst comprises between about 1 to about 10 grams of palladium, and about 0.5 to about 10 grams of gold per liter of catalyst, with the amount of gold being from about 10 to about 125 wt % based on the weight of palladium.

20. The composition of claim 14 wherein the alkali metal acetate is potassium acetate.

21. The composition of claim 14 wherein the alkali metal acetate is present in an amount of between about 10 and 70 grams per liter of catalyst.

22. The composition of claim 14 wherein the support material comprises particle support material or a ground support material.

23. A method of producing alkenyl alkanoates, comprising:

contacting a feed comprising an alkene, an alkanoic acid and an oxidizer to a catalyst or pre-catalyst comprising calcined palladium, calcined rhodium, gold and an alkali metal acetate on a support material.

* * * * *